(12) United States Patent
Averkiou et al.

(10) Patent No.: US 7,753,850 B2
(45) Date of Patent: Jul. 13, 2010

(54) METHOD FOR ULTRASOUND PERFUSION IMAGING

(75) Inventors: Michalakis Averkiou, Kirkland, WA (US); Patrick G. Rafter, Windham, NH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 735 days.

(21) Appl. No.: 10/576,997

(22) PCT Filed: Nov. 1, 2004

(86) PCT No.: PCT/IB2004/003570

§ 371 (c)(1),
(2), (4) Date: Apr. 25, 2006

(87) PCT Pub. No.: WO2005/044108

PCT Pub. Date: May 19, 2005

(65) Prior Publication Data

US 2007/0167797 A1 Jul. 19, 2007

Related U.S. Application Data

(60) Provisional application No. 60/518,277, filed on Nov. 7, 2003.

(51) Int. Cl.
*A61B 8/00* (2006.01)

(52) U.S. Cl. .................. 600/458; 600/437; 600/438; 424/9.5; 424/9.52

(58) Field of Classification Search .......... 600/458, 600/437, 439; 424/9.1, 9.5–9.52
See application file for complete search history.

(56) References Cited

U.S. PATENT DOCUMENTS

| | | | | |
|---|---|---|---|---|
| 5,456,257 A | * | 10/1995 | Johnson et al. | 600/458 |
| 5,474,073 A | * | 12/1995 | Schwartz et al. | 600/456 |
| 5,485,842 A | * | 1/1996 | Quistgaard | 600/443 |
| 5,577,505 A | * | 11/1996 | Brock-Fisher et al. | 600/458 |
| 5,706,819 A | * | 1/1998 | Hwang et al. | 600/458 |
| 5,720,291 A | * | 2/1998 | Schwartz | 600/456 |
| 5,833,613 A | * | 11/1998 | Averkiou et al. | 600/440 |
| 5,860,931 A | * | 1/1999 | Chandler | 600/458 |
| 5,908,389 A | * | 6/1999 | Roundhill et al. | 600/443 |
| 5,944,666 A | * | 8/1999 | Hossack et al. | 600/458 |
| 5,980,457 A | * | 11/1999 | Averkiou | 600/437 |
| 6,171,246 B1 | * | 1/2001 | Averkiou et al. | 600/458 |
| 6,251,074 B1 | * | 6/2001 | Averkiou et al. | 600/447 |
| 6,340,348 B1 | * | 1/2002 | Krishnan et al. | 600/447 |
| 6,468,216 B1 | * | 10/2002 | Powers et al. | 600/443 |
| 6,491,633 B1 | * | 12/2002 | Krishnan et al. | 600/447 |
| 2002/0040188 A1 | * | 4/2002 | Averkiou | 600/458 |
| 2002/0040189 A1 | * | 4/2002 | Averkiou et al. | 600/458 |

FOREIGN PATENT DOCUMENTS

WO    WO 2004/041091 A1    5/2004

* cited by examiner

*Primary Examiner*—Brian Casler
*Assistant Examiner*—Parikha S Mehta
(74) *Attorney, Agent, or Firm*—W. Brinton Yorks, Jr.

(57) ABSTRACT

An ultrasound imaging system transmits a broad beam of ultrasound into tissues that are perfused with blood containing microbubbles. The ultrasound has an intensity that is sufficient to destroy the microbubbles in the tissues. A plurality of ultrasound imaging beams are then transmitted into the tissues over a sufficient period to allow the tissues to re-perfuse, and reflections from the transmitted imaging beams are processed to provide a perfusion image. The transmitted microbubble-destroying ultrasound may be in the form of a single beam or a plurality of beams that insonify a substantially larger area than the area insonified by the transmitted imaging beams. As a result, the microbubbles are all destroyed at substantially the same time, and the imaging ultrasound is transmitted only into regions of the tissues from which ultrasound reflections will be received.

7 Claims, 5 Drawing Sheets

METHOD FOR ULTRASOUND PERFUSION IMAGING

CROSS REFERENCE TO RELATED APPLICATION

This application claims the benefit of U.S. provisional application Ser. No. 60/518,277 filed Nov. 7, 2003, which is incorporated herein.

This invention relates to ultrasound imaging systems, and, more particularly, to a system and method for obtaining ultrasound perfusion images in a manner that provides more rapid and accurate depictions of tissue perfusion and its quantification.

Ultrasound imaging systems are widely used to obtain a variety of ultrasound images. The imaging systems may be used to scan different parts of the body using a variety of different techniques or imaging modalities. For example, an ultrasound scanhead may transmit ultrasound into tissues beneath the scanhead and detect ultrasound reflections from the tissues from several different directions. The resulting image, known as a compound ultrasound image, can provide more accurate depictions of curved surfaces, and it has relatively little speckle. Harmonic ultrasound imaging can be performed by transmitting ultrasound energy having a fundamental frequency and detecting ultrasound reflections from tissues beneath a scanhead at harmonic frequencies. For either compound imaging or harmonic imaging, as well as conventional imaging, the scanhead may be scanned across tissues of interest to provide an extended field of view or panoramic image.

Ultrasound images depicting blood flow can be enhanced by the use of ultrasonic contrast agents. In contrast agents, gases, in the form of tiny bubbles called "microbubbles" are injected into the bloodstream of a patient. Microbubbles present a significant acoustic impedance mismatch in the body, thereby reflecting transmitted ultrasound to a significantly greater degree than red blood cells. As a result, microbubbles are conventionally used as contrast agents to improve the definition of blood flow. Microbubbles are typically small bubbles of gas coated with a thin biodegradable coating or shell. These coated microbubbles typically have diameters between 0.1 and 4.0 microns and a specific density about $1/10$ of the density of water. Coated microbubbles are normally suspended in an aqueous solution for infusion into the blood stream. Coated microbubbles have the advantage of being stable in the body for a significant period of time, as the shells serve to protect the gases of the microbubbles from diffusion into the bloodstream. The size of the microbubbles may be chosen to enable the microbubbles to pass through the capillary bed in the body. Therefore, microbubble contrast agents, whether coated or uncoated, can be used for imaging the body's vascularized tissues, such as the walls of the heart, since the contrast agent can be injected into the bloodstream and will pass through veins, arteries and capillaries with the blood supply until filtered from the blood stream in the lungs, kidneys and liver.

Although coated and uncoated microbubbles can survive in the body for an extended period, they can also be selectively destroyed. More specifically, at moderately high sound pressure amplitudes within FDA limits, acoustic pressure waves can cause microbubbles to rupture, freeing the gas to quickly diffuse into the bloodstream.

Contrast agents are frequently used in perfusion studies to assess the ability of vasculature to replenish tissue with a new supply of blood. Two types of perfusions studies are known as "high MI" studies and "low MI" studies, where MI refers to the mechanical index (intensity) of the transmitted acoustic pressure wave. In high MI studies, a series of high MI triggered image frames are acquired. The high MI pulses of the image frames are synchronized to the heart cycle with an EKG gate, respiratory gate or other gating (triggering) signal so that the resultant image will brightly show the amount of bloodflow which has reperfused tissue since the previous image frame. The image is formed with the microbubble destruction signals and shows the location of microbubbles at the time of destruction. The intensity of the image is proportional to the destruction events. See for example U.S. Pat. No. 5,457,257 (Johnson et al.) which describes a differential two-pulse high MI technique. In low MI studies the imaging pulses have small amplitudes such that the microbubbles are not destroyed and there is no need for triggering the transmit signals. For quantification of blood flow in the microcirculation an initial high MI frame referred to as a "flash" frame is transmitted to destroy the microbubbles currently in the tissue of the image. After the microbubbles in a region of interest have been destroyed, the blood that contained the destroyed microbubbles flows out of tissues in the region of interest, and new blood containing microbubbles re-perfuses these tissues. Ultrasound pulses having magnitudes that are insufficient to destroy microbubbles in the blood re-perfusing the tissues are then periodically transmitted into the region of interest, and resulting echo signals are obtained. As the density of the microbubbles increases with the re-perfusion of the tissues with blood containing microbubbles, the intensity of echoes from the region of interest increases. The manner in which the intensity of the echoes increases provides an indication of tissue perfusion, which can be seen in the low MI images produced from these echoes. A low rate of tissue perfusion in certain areas may provide an indication of abnormal medical condition, such as, for example, a blockage of blood flow in the heart. By depicting tissue reperfusion in this manner on a spatial basis, a parametric image can be obtained which shows the perfusion rate at various locations in tissues being imaged. For example, an image may be obtained showing a cross-section of the left ventricle that has been color-coded to show the perfusion rate in the myocardium, i.e., the walls of the left ventricle.

One conventional technique for obtaining ultrasound perfusion images is shown in FIG. 1. A phased array transducer 10 sequentially transmits several high intensity beams 12a-n of ultrasound into vascularized tissues 14 of interest. The intensity of the ultrasound is sufficient to break or destroy microbubbles in the area of the tissues 14 that is insonified by each beam 12a-n. The transducer 10 thereafter transmits several beams 12a-n of ultrasound having an intensity that is insufficient to destroy microbubbles in the insonified tissues 14. This relatively low intensity ultrasound is reflected by the microbubbles which have re-entered the tissues 14, and the reflections are received by the transducer 10. The low intensity ultrasound is repetitively transmitted and resulting ultrasound reflections detected over a sufficient period of time for the tissues to re-perfuse, and the detected ultrasound is used to generate a series of ultrasound perfusion images.

One problem with the technique shown in FIG. 1 is that it can take a considerable period to destroy all of the microbubbles in the tissues 14. More specifically, the microbubbles in the tissues 14 insonified by the beam 12a are destroyed first followed by the microbubbles insonified by the beam 12b, and so forth, until the microbubbles insonified by the beam 12n are finally destroyed. This beam-by-beam destruction of microbubbles is especially disadvantageous when doing three dimensional (3D) imaging, where the time required to transmit many beams over a volume of tissue can take an appreciable amount of time. As a result, the 3D frame rate can be significantly degraded. Another problem is uneven microbubble destruction at different depths. The depth where the high intensity beams come into focus will experience greater acoustic pressures than shallower or deeper depths, resulting in greater microbubble destruction in the focal region. A more uniform destruction at all depths would be more desirable for better reperfusion imaging and quantification.

The problems caused by the uneven destruction of microbubbles using the technique shown in FIG. 1 has been addressed by using another technique that will be explained with reference to FIG. 2. A phased array transducer 20 transmits a single plane wave beam 22 of ultrasound energy having an intensity that is sufficient to destroy the microbubbles in vascularized tissues 24 insonified by the beam 22. For high MI imaging a series of high MI plane waves are transmitted and the returning echo signals beamformed to produce a sequence of high MI images. For low MI imaging a series of low MI plane waves are transmitted, and the returning echoes are beamformed to produce a sequence of low MI images. While this technique addresses the aforementioned problems, it suffers from low resolution and imprecise quantification due to the lack of any focused transmit beam formation and resultant high side lobe levels. Moreover, while the technique performs well for steady state flow analysis, it does not address the needs of quantified reperfusion studies.

There is therefore a need for a system and method that can accurately depict blood perfusion in tissues, and provides high accuracy and speed in quantified reperfusion studies.

A method and system for obtaining an ultrasound perfusion image of tissues perfused with blood containing microbubbles includes an ultrasound scanhead having a one-dimensional transducer array or a two-dimensional transducer array. Signals are applied to the scanhead to cause it to transmit at least one broad beam of ultrasound into the tissues having an intensity that is sufficient to destroy microbubbles in the tissues that are insonified by the ultrasound. This broad beam of microbubble-destroying ultrasound encompasses a first area of the tissues, and echoes from the broad beam may or may not be used for imaging purposes. Signals are also applied to the scanhead to cause it to repetitively transmit a plurality of beams of imaging ultrasound into the tissues. This transmitted imaging ultrasound has a relatively low intensity and thus do not destroy microbubbles in the tissues that are insonified by the imaging ultrasound beams. Each beam of imaging ultrasound that is transmitted has a second area that is smaller than the first area insonified by the microbubble destroying ultrasound. The scanhead receives reflections from each of the transmitted imaging ultrasound beams in respective receive beams, and each of these receive beams also has an area that is smaller than the area of the microbubble destroying beams. The scanhead transmits ultrasound imaging beams and receives reflections from the transmitted imaging beams over a period that is sufficient to allow re-perfusion of the tissues. A processor processes the received reflections and interfaces with a display to provide an ultrasound perfusion image.

Embodiments of the present invention are directed to ultrasound imaging systems. Certain details are set forth below to provide a sufficient understanding of various embodiments of the invention. However, it will be clear to one skilled in the art that the invention may be practiced without these particular details. In other instances, well-known circuits, control signals, and timing protocols have not been shown in detail in order to avoid unnecessarily obscuring the invention.

Figure 2:
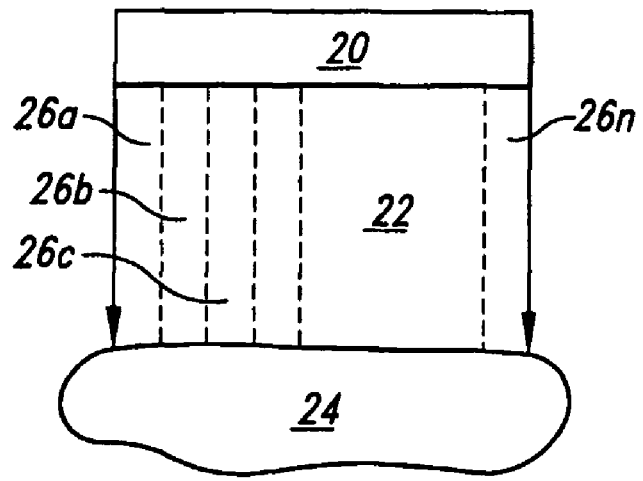
FIG. 2 is a schematic view illustrating another technique that is conventionally used for ultrasound perfusion imaging.
Figure 3A:
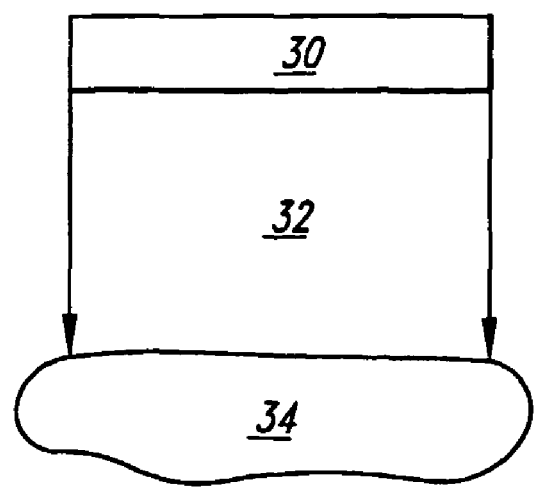
FIGS. 3A and 3B are schematic views illustrating a technique for ultrasound perfusion imaging according to one embodiment of the invention.
Figure 3B:
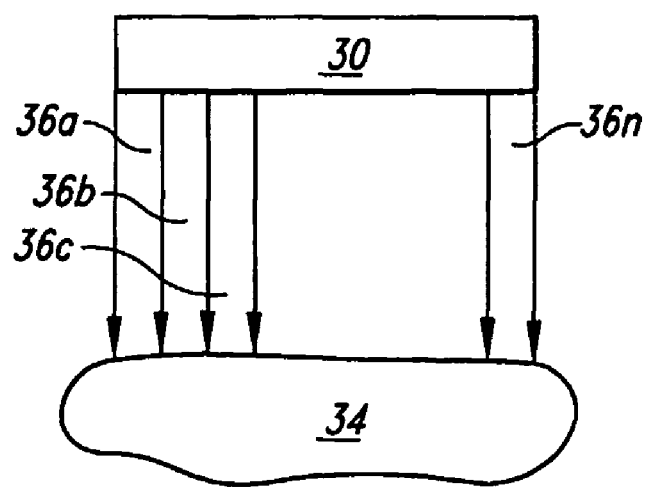

One embodiment of a technique for ultrasound perfusion imaging in accordance with the invention is shown in FIGS. 3A and 3B. With reference to FIG. 3A, a phased array transducer 30 transmits a single broad or plane wave beam 32 of ultrasound energy having an intensity that is sufficient to destroy microbubbles in vascularized tissues 34 insonified by the beam 32. As a result, re-perfusion of the entire area of interest in the tissues 34 starts at the same time. However, unlike the technique of FIG. 2, a plurality of single plane wave beams of low intensity ultrasound energy are not used for imaging purposes. Instead, as shown in FIG. 3B, the transducer 30 transmits several beams 36a-n of ultrasound having an intensity that is insufficient to destroy microbubbles in the insonified tissues 34. This relatively low intensity ultrasound is reflected by the microbubbles in the tissues 34, and the reflections are received by the transducer 30 in receive beams 36a-n that coincide with the beams 36a-n of transmitted ultrasound. As a result, the transmitted ultrasound is directed only into areas of the tissues 34 that coincide with the areas from which ultrasound reflections are detected. Consequently the round-trip beam profile of the imaging ultrasound is well focused and resolved, enabling the production of high resolution images and precise reperfusion quantification.

Figure 4A:
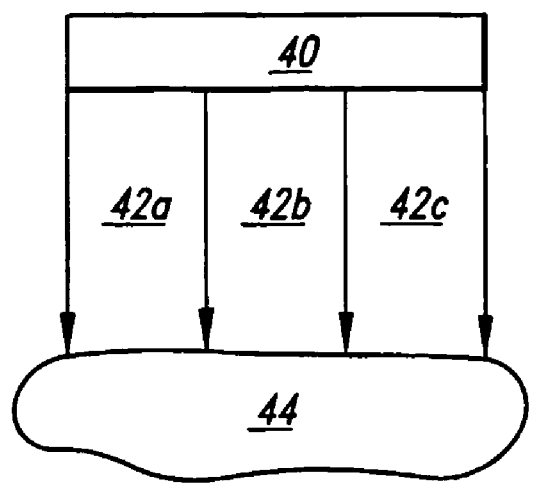
FIGS. 4A and 4B are schematic views illustrating a technique for ultrasound perfusion imaging according to another embodiment of the invention.
Figure 4B:
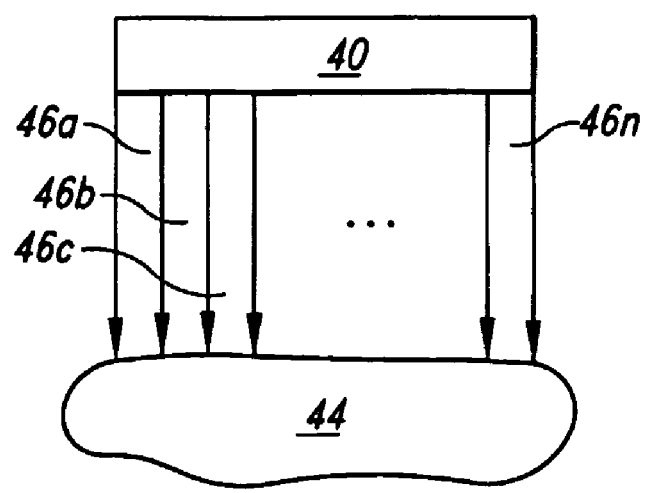

In another embodiment of the invention illustrated in FIG. 4A, a phased array transducer 40 sequentially transmits several high intensity broad ultrasound beams 42a-c into vascularized tissues 44 beneath the transducer 40 to destroy microbubbles in areas of the tissues 44 insonified by the beams 42a-c. Thereafter, as shown in FIG. 4B, ultrasound imaging beams 46a-n of low intensity (to avoid microbubble destruction) are sequentially transmitted, and ultrasound reflections are detected in received imaging beams 46a-n that coincide with the transmitted imaging beams 46a-n in the same manner as shown in FIG. 3B. The embodiment of FIGS. 4A and 4B has the disadvantage of destroying the microbubbles in the tissues 44 at different times. However, since only a few microbubble-destroying beams 42a-c are used, the microbubbles insonified by each of the beams 42a-c are destroyed at times that are sufficiently close to each other that tissue perfusion can be accurately portrayed. The use of microbubble-destroying beams 42a-c that are significantly wider than the transmitted imaging beams 46a-n thus causes the microbubbles to be destroyed at essentially the same time, and the resultant echoes may or may not be used for imaging depending upon the needs of the user.

The quick destruction of the microbubbles is also aided by the rapid rate at which the microbubble-destroying beams 42a-c can be transmitted. Specifically, the microbubble-destroying beams 42a-c can be transmitted at a high rate because it is not necessary to wait for reflections from one transmitted beam 42a-c to reach the transducer 40 before the next beam 42a-c can be transmitted. Since it is not necessary to wait for returning echo signals in this embodiment before transmitting the next microbubble-destroying beam, the microbubble-destroying beams can be transmitted in a burst in rapid, immediate succession along the transducer aperture.

Figure 1:
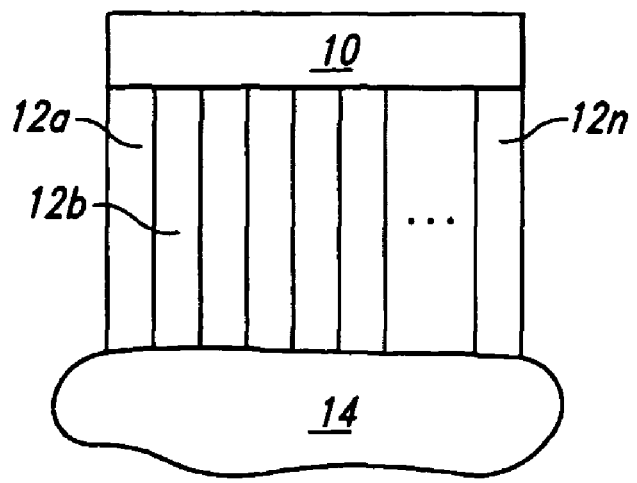
FIG. 1 is a schematic view illustrating one technique that is conventionally

By comparison, in the technique illustrated in FIG. 1, the second microbubble-destroying beam 12b cannot be transmitted until reflections from the first imaging beam 12a have been received. It is primarily for this reason, that the prior art technique shown in FIG. 1 cannot destroy all of the microbubbles at substantially the same time. In distinction, using the technique shown in FIGS. 4A and 4B, the microbubble-destroying beams 42a-c can be transmitted right after each other. This technique of rapid firing may generally be performed by standard imaging systems without the need for extensive modifications.

Figure 5A:
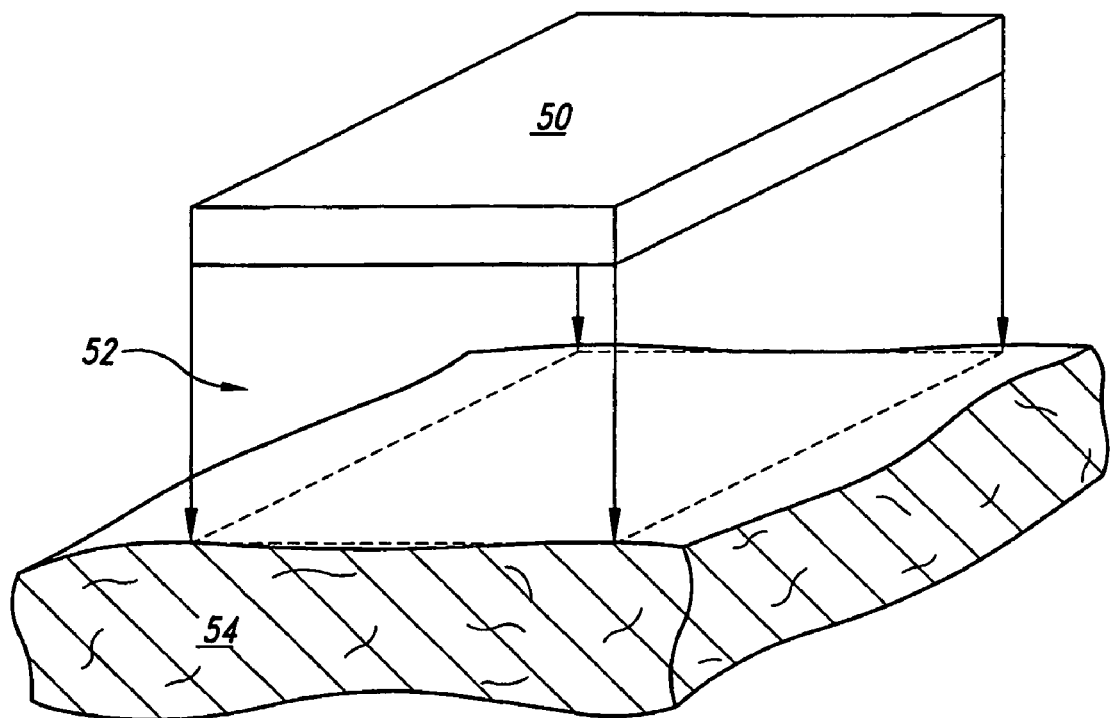
FIGS. 5A and 5B are schematic views illustrating a technique for generating a three-dimensional or volume ultrasound perfusion image according to one embodiment of the invention.

The perfusion imaging techniques shown in FIGS. 3A, 3B and 4A, 4B use one-dimensional transducer arrays that generate a beam that is used for two-dimensional B-scan perfusion imaging. It will be appreciated that the imaging beams of the embodiments described may be steered in a linear, sector, or steered linear pattern, using a phased array, linear array, curved array or other transducer format. In a similar manner to the preceding embodiments, a 2-dimensional transducer array can be used to generate beams that can be used for three-dimensional or volume perfusion imaging. With reference to FIG. 5A, a two-dimensional transducer array 50 transmits a single, two-dimensional plane-wave beam 52 into vascularized tissues 54 containing microbubbles. The transmitted beam 52 has sufficient power to destroy all of the microbubbles in the tissue volume 54. Thus, all of the microbubbles in the tissues are destroyed at the same time. In another embodiment of the invention, rather than using a single microbubble-destroying beam 52, separate two-dimensional plane-wave beams, e.g., three beams, are transmitted into the tissues 54 in a manner analogous to the use of separate one-dimensional microbubble-destroying beams 42 as shown in FIG. 4A. The use of separate microbubble-destroying beams transmitted either sequentially or simultaneously enables the selection and control of microbubble-destruction in different subvolumes in front of the transducer aperture. The microbubble-destroying beams can be differently steered to destroy microbubbles in differently angled subvolumes, for instance.

Figure 5B:
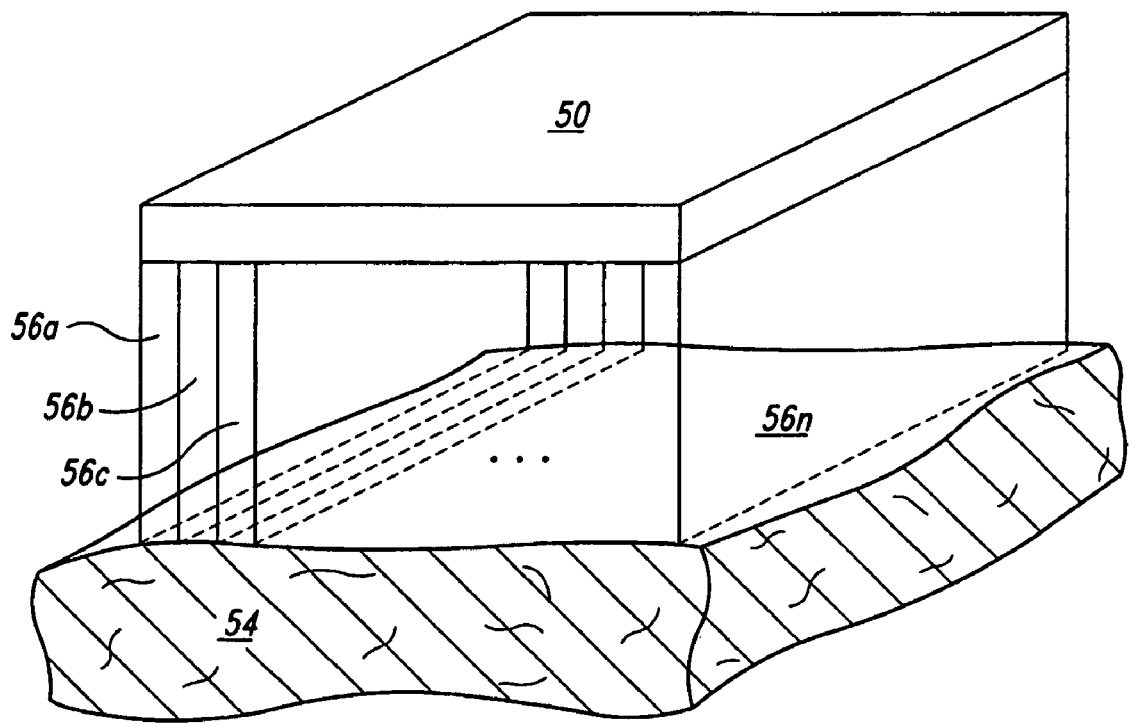

Regardless of whether a single microbubble-destroying beam or multiple microbubble-destroying beams are used, after the microbubbles have been destroyed, the two-dimensional transducer array 50 transmits a series of imaging beams 56a-n as shown in FIG. 5B. After each imaging beam 56a-n is transmitted, reflections from the tissues 54 and microbubbles in the re-perfused tissues 54 are detected in received imaging beams 56a-n that are coincident with the transmitted imaging beams 56a-n. The received imaging beams 56a-n are then processed to provide a three-dimensional or volume image showing the rate of perfusion in the tissues 54. It will be understood that the present invention can also be practiced with multiline systems, in which the imaging beams comprise a "fat" transmit beam or multiple, simultaneous differently steered transmit beams followed by the reception of multiple simultaneous receive beams for imaging. Multiple microbubble-destroying beams can also be transmitted simultaneously with a multiline transmitter. These multiple microbubble-destroying beams can all be steered in the same direction, e.g., straight ahead, or can be steered in different transmit directions or angles. For example, three microbubble destroying beams can be transmitted at the same time, with one transmitted at an angle to the transducer of −20°, a second transmitted at an angle of 0°, and a third transmitted at an angle of +20°.

The area or volume of microbubble destruction can be controlled in several ways. One is to change the focusing of the microbubble destruction beams. A beam can be an unfocused plane wave or a weakly focused beam with a focal point below the maximum depth of the image, or a more strongly focused beam. Another way to control the microbubble destruction region is by changing the aperture size, that is, transmitting with fewer or a greater number of transducer elements of the array transducer. A third way to control the microbubble destruction region is by control of the transmit apodization, that is, the weighting functions applied to the transmit channels of the transmit aperture. These area or volume control techniques can be used together in various combinations.

In a constructed embodiment of the present invention, either unfocused destruction beams or weakly focused destruction beams (where the focus is placed in the far field, beyond the maximum image depth) or combinations thereof may be employed. Unfocused beams do not use delays between different elements of the array transducer and weakly focused beams only use small delays between element or between only a small number of elements. Also, although the microbubble-destroying beams, as well as the transmitted and received imaging beams in the illustrated embodiments are not shown steered from side to side, it will be understood that steered beams may alternatively be used. Finally, perfusion imaging in other embodiments of the present invention may be performed in combination with other ultrasound imaging techniques, such as compound imaging, tissue harmonic imaging, Doppler flow imaging, and panoramic imaging, to name a few.

Figure 6:
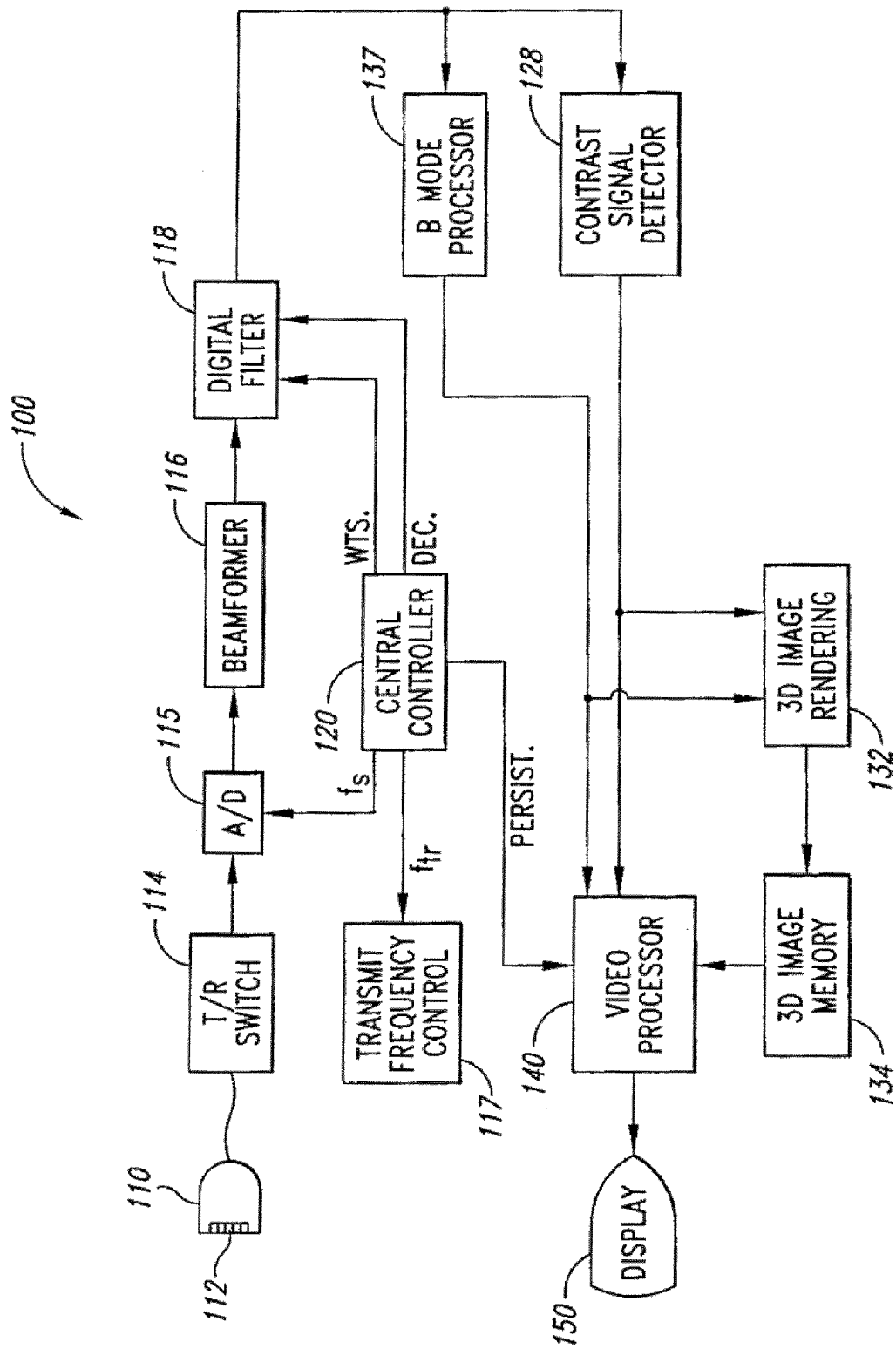
FIG. 6 is a block diagram of an imaging system that can be used for ultrasound perfusion imaging using the technique shown in FIGS. 3-5.

One embodiment of an ultrasonic diagnostic imaging system 100 that can generate perfusion images using the embodiments shown in FIGS. 3-5, as well as other embodiments of the invention, is shown in FIG. 6. The imaging system 100 includes an ultrasound scanhead 110 having a two-dimensional transducer array 112 that transmits ultrasonic energy and receives echoes in response to the ultrasound transmission. For imaging microbubbles, nonlinear imaging techniques are often desirable. In the event harmonic imaging is used, the response characteristic of the transducer can exhibit two passbands, one around the central transmit frequency and another about the center of the received passband. For imaging harmonic contrast agents, a broadband transducer having a passband encompassing both the transmit and receive passbands may be used. Pulse inversion and amplitude modulation techniques may be used for harmonic separation, such as those described in U.S. Pat. No. 5,706,819 (Hwang) and U.S. Pat. No. 5,577,505 (Brock-Fisher).

The imaging system 100 also includes a central controller 120 that provides a control signal $f_{tr}$ to a transmit frequency control circuit 117 to control the center frequency and time of transmission of the transmitted ultrasound. The transmit frequency control circuit 117 pulses the elements of the transducer array 112 by means of a transmit/receive switch 114. As explained above with reference to FIGS. 3-5, the transducer array 112 is initially pulsed in one or more microbubble-destroying bursts followed by transmission of a relatively large number of imaging beams.

Echoes received by the transducer array 112 from a relatively large number of received imaging beams are coupled through the T/R switch 114 and digitized by analog-to-digital ("A/D") converters 115. The sampling frequency $f_s$ of the A/D converters 115 is controlled by the central controller 120. The desired sampling rate is dictated by sampling theory and is at least twice the highest frequency $f_c$ of the received passband. Sampling rates higher than the minimum requirement are also desirable.

The transmitting and receiving of imaging beams is repeated at intervals that allow time for blood containing microbubbles to gradually infuse the vessels and tissues of interest. The frame rate of these transmissions can be on the order of one-thirtieth of a second, and can be gated to the heart rate. In any case, the samples of signals from the transducer array 112 are delayed and summed by a beamformer 116 to form coherent echo signals. The digital coherent echo signals are then filtered by a digital filter 118. In the embodiment of FIG. 6, the relationship between the transmit frequency $f_r$ and the received frequency is not fixed, and hence a band of frequencies may be received that is different from the transmitted band of frequencies. Thus, the received frequencies may be harmonics of the transmitted frequencies. The digital filter 118 bandpass filters the signals in a predetermined passband, and may also shift the frequency band to a lower or baseband frequency range.

The filtered signals from the digital filter 118 may be coupled to a B-mode processor 137 for conventional B-mode processing. Filtered echo signals of the contrast agent passband are coupled to a contrast signal detector 128, which eliminates stationary tissue signals by pulse-to-pulse subtraction of temporally discrete echoes from a given spatial location, amplitude or envelope detects the resulting difference signals, and discriminates for motion signal components on an amplitude basis. Simple two pulse subtraction of the form P1-P2 may be employed, where P1 represents the echoes received following one pulse and P2 represents the echoes received following another pulse. Alternatively the contrast agent may be detected by B-mode processing or Doppler processing.

Respective outputs from the B-mode processor 137 and the contrast signal detector 128 are coupled to a 3D image rendering processor 132 for the rendering of three-dimensional images, which are stored in a 3D image memory 134. Three dimensional rendering may be performed as described in U.S. Pat. Nos. 5,720,291; 5,474,073 and 5,485,842, which are incorporated herein by reference. The signals from the contrast signal detector 128 and the B-mode processor 137, and the three dimensional image signals from the 3D image memory 134, are coupled to a video processor 140 where they may be selected for display on an image display 150 as dictated by user selection.

In operation, the perfusion image shown in the display 150 is able to accurately portray and quantify the reperfusion of tissues because all of the microbubbles in the tissues are destroyed at essentially the same time. The use of focused and/or weakly focused beams for imaging results in good resolution in the resultant contrast images.

Although FIG. 6 illustrates one embodiment of the invention, it will be understood that different embodiments may be used, and components may be added to or subtracted from the components shown in FIG. 6 to provide an imaging system that is capable of providing ultrasound perfusion images in accordance with the various embodiments disclosed herein or hereafter developed. According, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of obtaining an ultrasound perfusion image of tissues perfused with blood containing microbubbles, the method comprising:
   transmitting a plane wave of microbubble-destroying ultrasound into the tissues, the plane wave of microbubble-destroying ultrasound encompassing a first area of the tissues, the microbubble-destroying ultrasound having an intensity that is sufficient to destroy microbubbles in the tissues that are insonified by the microbubble-destroying ultrasound;
   repetitively transmitting a plurality of beams of imaging ultrasound into the tissues, wherein each beam of imaging ultrasound insonifies a second area of tissue within the first area, and wherein each second area is smaller than the first area, the imaging ultrasound having an intensity that is substantially insufficient to destroy microbubbles in the tissues that are insonified by the imaging ultrasound;
   receiving reflections from each of the transmitted imaging ultrasound beams in respective receive beams, wherein each of the receive beams is received from a third area of tissue within the first area, and wherein each third area is smaller than the first area; and
   processing the received reflections over a sufficient period to allow re-perfusion of the tissues to provide an ultrasound perfusion image.

2. The method of claim 1 wherein the act of transmitting a plane wave of microbubble-destroying ultrasound into the tissues comprises transmitting a single plane wave of microbubble-destroying ultrasound into the tissues.

3. The method of claim 1 wherein the act of transmitting a plane wave of microbubble-destroying ultrasound into the tissues comprises transmitting a sequence of plane waves of microbubble-destroying ultrasound into the tissues.

4. The method of claim 1 wherein the act of repetitively transmitting a plurality of beams of imaging ultrasound into the tissues and receiving reflections from each of the transmitted imaging ultrasound beams comprises transmitting the beams of imaging ultrasound into the tissues at a first frequency and receiving reflections from the transmitted imaging ultrasound beams at a second frequency that is a harmonic of the first frequency.

5. The method of claim 1 wherein the size of each second area insonified by a respective transmitted imaging beams is substantially equal to the size of the respective third area from which reflections from each of the transmitted imaging ultrasound beams are received.

6. A method of obtaining an ultrasound perfusion image of tissues perfused with blood containing microbubbles, the method comprising:
   using ultrasound to simultaneously destroy substantially all of the microbubbles in the tissues over a first area; and
   repetitively using ultrasound transmitted to and received from a plurality of second areas within the first area, wherein each of the second areas is smaller than the first area, and wherein the sum of the second areas substantially encompasses the first area to obtain an indication of the quantity of microbubbles in the tissues that are intact over a re-perfusion time, each of the second areas being smaller than the first area,
   wherein the act of using ultrasound to simultaneously destroy substantially all of the microbubbles in the tissues over a first area comprises using a plane-wave beam of ultrasound to simultaneously destroy substantially all of the microbubbles in the tissues over the first area.

7. The method of claim 6 wherein the act of using ultrasound to simultaneously destroy substantially all of the microbubbles in the tissues over a first area comprises using a broad beam of ultrasound to simultaneously destroy substantially all of the microbubbles in the tissues over the first area.

* * * * *